United States Patent [19]

Leighton et al.

[11] 4,321,915
[45] Mar. 30, 1982

[54] EVERTING TUBE DEVICE WITH RELATIVE ADVANCE CONTROL

[75] Inventors: Stephen B. Leighton, Silver Spring; William H. Boyd, Hyattsville, both of Md.

[73] Assignee: The United States of America as represented by the Department of Health and Human Services, Washington, D.C.

[21] Appl. No.: 217,143

[22] Filed: Dec. 16, 1980

Related U.S. Application Data

[63] Continuation-in-part of Ser. No. 52,110, Jun. 26, 1979, abandoned.

[51] Int. Cl.³ ................................................ A61B 1/00
[52] U.S. Cl. ....................................... 128/4; 128/658; 128/349 R
[58] Field of Search ................................ 128/4, 6–11, 128/348, 349 R, 349 B, 350 R, 351, 262, 630, 658

[56] References Cited

U.S. PATENT DOCUMENTS

| | | |
|---|---|---|
| 3,168,092 | 2/1965 | Silverman . |
| 3,332,424 | 7/1967 | Minteer . |
| 3,433,214 | 3/1969 | Silverman . |
| 3,525,329 | 8/1970 | Zeimer et al. . |
| 3,866,601 | 2/1975 | Russell . |
| 3,908,635 | 9/1975 | Viek . |
| 3,908,663 | 9/1975 | Viek . |
| 3,911,927 | 10/1975 | Rich et al. . |
| 4,040,413 | 8/1977 | Oshiro . |
| 4,077,610 | 3/1978 | Masuda . |
| 4,148,307 | 4/1979 | Utsugi . |

OTHER PUBLICATIONS

Zeimer et al., "Toposcopy–Frictionless Method of Entering Body Cavities", N.Y. State, J. of Med. (Jul. 15, 1965).

Primary Examiner—John D. Yasko
Attorney, Agent, or Firm—Browdy and Neimark

[57] ABSTRACT

An everting tube device for introducing an elongated tool into a body cavity through a body opening for diagnostic or other purposes comprises an elongated housing containing a folded evertable flexible tube through which an elongated tool, such as a fiber optic bundle, sealingly extends. The flexible tube can be everted from the housing by applying fluid pressure to the housing interior, and the eversion of the tube carries the tool along with it at twice the rate. The tool can be retracted by applying vacuum to the housing interior which draws the tube away from the tool. The alternate use of pressure and vacuum, along with the intermediate steps of manually retracting the tool, result in projecting the tool and tube into the appropriate cavity at substantially the same rate. When the tool used is a fiber optic bundle, it provides a means of continuously viewing the path of travel immediately ahead of the advancing tube.

11 Claims, 5 Drawing Figures

EVERTING TUBE DEVICE WITH RELATIVE ADVANCE CONTROL

This is a continuation-in-part of parent, copending application Ser. No. 52,110, filed June 26, 1979, now abandoned.

FIELD OF THE INVENTION

This invention relates to extensible body exploration probe devices, and more particularly to a probe device for introducing an elongated diagnostic tool or examination implement into a body cavity through a body opening.

BACKGROUND OF THE INVENTION

Various types of extensible probe devices have been proposed which employ a flexible envelope which can be extended or retracted by means of positive or negative fluid pressure. These probes generally are in the form of relatively long inwardly foldable flexible film-like tubes with suitable rigid housings normally containing the folded tubes and with means to apply fluid pressure to the housings for causing the film-like tubes to be extended from the housings into a body cavity or tract through a body opening, such as the mouth, nose, anus or urethra. These prior art devices may be used to locate a tool, such as a catheter, within the cavity, but do not seek to use the extensible film-like tubes for the purpose of closely controlling and advancing an elongated tool or diagnostic examination device, nor for efficiently feeding such a tool or diagnostic device, into the body cavity under study.

While devices described in prior patents include means for everting a flexible tubing element from a rigid housing into a body passage and thereby inserting a relatively long section of everted tubing into the body passage under study, none of such devices provides for examination of the path ahead of the tubing as it is being advanced along the passageway. Where an interior element such as a tool, e.g. a fiber optic scope, is inserted along with the tube, in the prior art devices, the distance the tool is to travel before it is available for use must be predetermined because the tool moves 2x the rate of the everting tube, and therefore such element must be placed far back within the everting tube at the start, and cannot be used except when the whole assembly is extended the predetermined length.

SUMMARY OF THE INVENTION

In contrast to the devices of the prior art, the apparatus of the present invention comprises a safe and effective means to introduce a flexible fiber optic bundle and/or tubes and assorted tools into body cavities through body openings such as the mouth, nose, anus and urethra. The device of the present invention supports the forward end of a central element, such as a fiber optic bundle or other tool, at or near the folded edge of an everting tube. This enables the fiber optic bundle to be employed for examining the portion of the insertion channel near or immediately ahead of the folded edge as it progresses forwardly along said channel. Therefore the device permits continuous examination of the path in front of the everting tube. Because the device can be manipulated to grasp and release the tool sequentially, the tool can be moved at the same rate as the everting tube without being subject to the 2x movement rate.

Accordingly, an object of the invention is to overcome the deficiencies and disadvantages of the prior art everting tube devices, such as indicated above.

Another object is to provide for the improved and more comfortable examination or treatment of body cavities of patients.

Yet another object is to provide an improved everting tube apparatus.

A further object of the invention is to provide an improved everting tube device for moving an elongated diagnostic or tool element through a body passage with relative advance control of the element with respect to the associated everting tube.

A still further object of the invention is to provide an improved everting tube device for inserting a central fiber optic bundle or elongated central tool element into a body passage by means of the alternate use of fluid pressure and suction, wherein the folded edge of the everting tube can be maintained rearwardly adjacent to the front end of the fiber optic bundle or tool element.

A still further object of the invention is to provide an improved everting tube device for inserting an elongated central element into a body cavity through a body opening, wherein the advance of the central element can be accurately controlled as it progresses into the cavity.

A sill further object of the invention is to provide an improved device for introducing a flexible fiber optic bundle into a body cavity, wherein the path of insertion immediately ahead of the device can be continuously examined.

A still further object of the invention is to provide an improved fluid pressure system for inserting an evertible tube and a central fiber optic bundle into a body cavity, utilizing alternate fluid pressure and suction applied to the evertible tube, with intervening small retractions of the central fiber optic bundle so as to keep the forward end of the bundle a small distance ahead of the folded edge of the evertible tube.

A still further object of the invention is to provide an improved everting tube device for inserting an elongated diagnostic device or other central tool into a body cavity, wherein the everting tube element is employed for the purpose of closely controlling and advancing the tool or diagnostic device and for efficiently feeding it into the body cavity under study.

BRIEF DESCRIPTION OF THE DRAWINGS

Further objects and advantages of the invention will become apparent from the following description and claims, and from the accompanying drawings, wherein:

DESCRIPTION OF A PREFERRED EMBODIMENT

Figure 1:
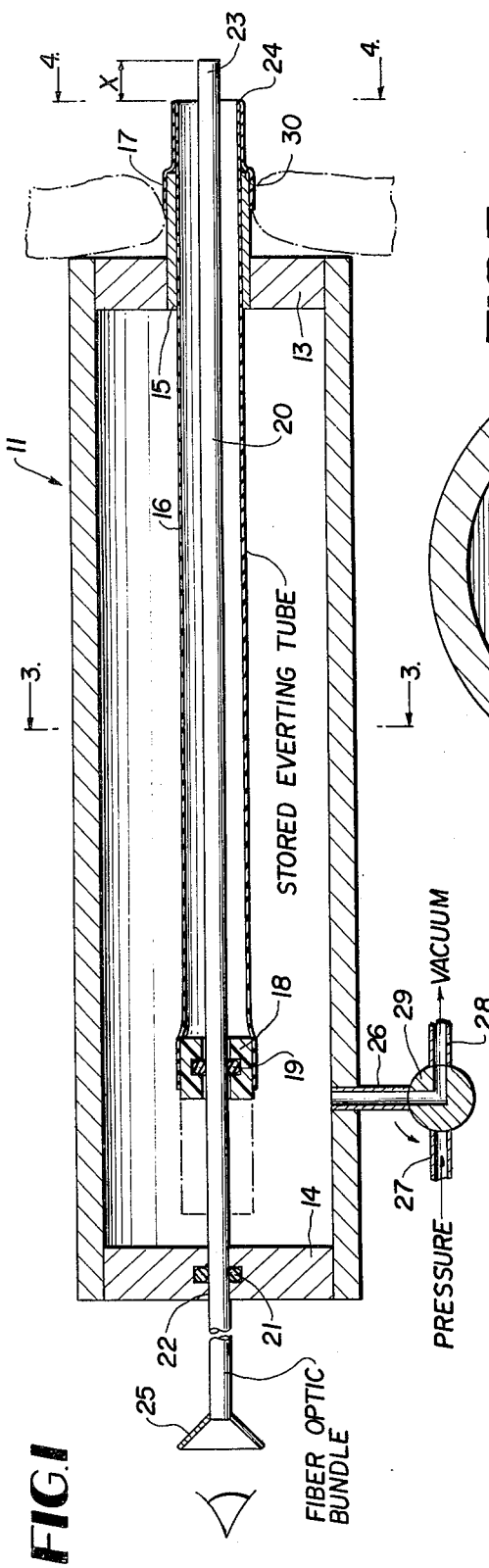
FIG. 1 is a diagrammatic longitudinal vertical cross-sectional view taken through an improved everting tube device constructed in accordance with the present invention, shown with its central diagnostic tool element partly advanced, and in a position released by vacuum applied to the device.

Referring to the drawings, a typical extensible probe device 11 according to the present invention is shown in FIG. 1. The device 11 comprises an elongated cylindrical chamber or housing 12 suitably formed of a sterilizable material, e.g. stainless steel or polycarbonate plastic, and having a circular forward end wall 13 and a rear circular end wall 14. The forward end wall 13 has a central aperture in which is rigidly secured an axial forwardly projecting rigid support tube 15 preferably of thin wall tubing, e.g. stainless steel of 25 mils wall thickness. An elongated flexible thin film-like everting tube 16, e.g. of substantially non-elastic transparent polyurethane of 15 mils thickness, has its forward end portion permanently secured on the front portion of support tube 15 at 17 and is folded inwardly around the front rim 30 of support tube 15 and extends rearwardly through tube 15 into the interior of housing 12.

The inner end of the everting tube 16 is permanently secured around a sealing bushing 18, e.g. of nylon, provided with an inner annular groove containing an O-ring 19 of resilient deformable sealing material, e.g. neoprene. A central elongated tool member 20, such as a fiber optic bundle or other type of tool member, extends axially through the bushing 18 and is sealingly and slidably engaged by the O-ring 19. The tool member 20 is also sealingly and slidably engaged by another O-ring 21, e.g. neoprene, mounted in an annular groove formed in a central aperture 22 in rear end wall 14.

In the typical embodiment shown in FIG. 1 the elongated tool member 20 is a fiber optic bundle whose forward end tip 23 may initially be located slightly behind the annular front fold 24 of the everting tube 16, and whose rear end is provided with an eyepiece 25 for viewing the region ahead of the annular fold 24 during the insertion of the tool 20 into a body passage. The fiber optic bundle 20 may be conventionally provided with a suitable illuminating light source, not shown. The elongated chamber 12 is provided with a fluid connection conduit 26. A fluid pressure conduit 27 and a vacuum conduit 28 are selectively connected through a two-way valve 29 to the conduit 26.

In an actual embodiment constructed of size suitable for urethral use, the housing 12 was about 28 inches long and formed of acrylic plastic, with the end walls 13 and 14 formed of nylon. The flexible everting tube 16 was about 22 inches long permitting an extension of about 11 inches, and was formed of clear polyurethane with a diameter of 3/16 inches and a wall thickness of 15 mils. The O-rings 19 and 21 were conventional neoprene O-rings (Parker-Hannifin #2-003). A commercial soap solution was used as a lubricant on the tool during testing, although for clinical use a medically acceptable lubricant such as KY jelly is used to avoid tissue irritation.

Figure 2:
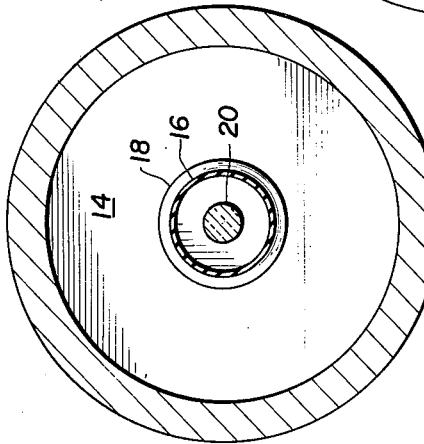
FIG. 2 is an enlarged fragmentary vertical longitudinal view illustrating how the everting tube is forced against the central tool element by fluid pressure applied to the device, to thereby grip the tool element and advance it concurrently with the everting movement.
Figure 3:
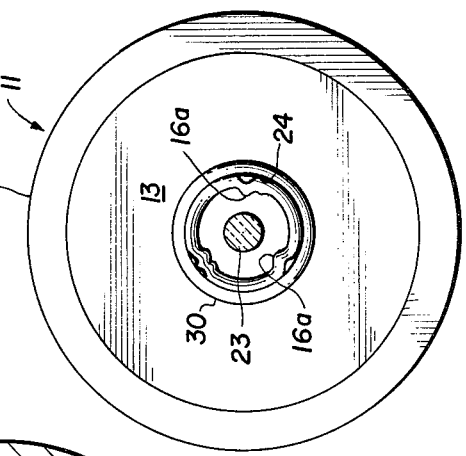
FIG. 3 is an enlarged transverse vertical cross-sectional view taken substantially on line 3—3 of FIG. 1.
Figure 5:
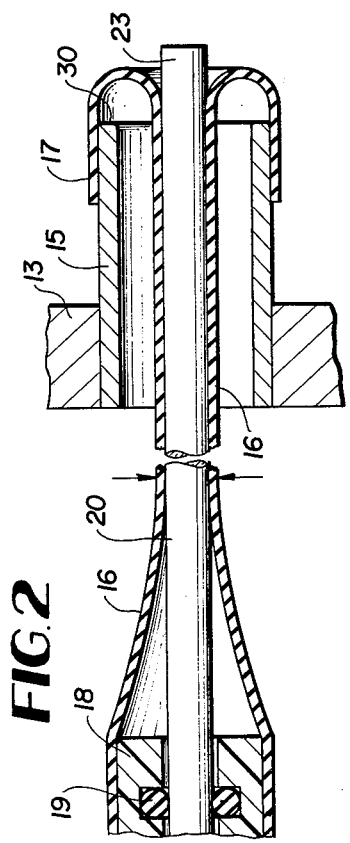
FIG. 5 is an enlarged fragmentary longitudinal vertical cross-sectional view through the forward portion of the device showing the relative positions of the tool tip and the annular fold of the everting tube prior to a pressurizing step in a typical tool insertion procedure as described herein.

In operation, the everting tube 16 normally loosely surrounds the tool element 20. The front member 15, with the annular fold of the everting tube extending around its front rim and with the tool tip 23 located slightly behind said fold 24 as generally shown in FIG. 5, is inserted into a body opening leading to the body passage or cavity under study, and the valve 29 is operated so as to connect the fluid pressure conduit 27 to the chamber connection conduit 26. Fluid under pressure is thus applied to the interior of chamber 12 and is introduced into the interior of the annular fold of the tube 16. This causes the flexible tube 16 to tightly grip the tool 20, as shown in FIG. 2, and drives forward and everts the forward end portion of the tube 16 forwardly from the front rim 30 of rigid support tube 15, carrying the tool tip 23 forwardly at a rate twice that of the rate of forward movement of the annular fold 24, namely, through a distance X shown in FIG. 1. This application of fluid pressure may be continued, when the tool incorporates a fiber optic viewing device, for a duration sufficient to provide a convenient initial viewing position of the tip 23, for example, a position providing a view of the region in the body passage immediately ahead of the tip.

Figure 4:
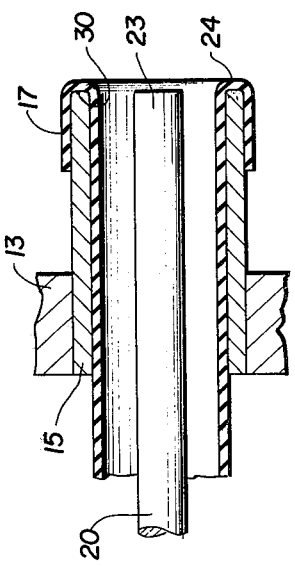
FIG. 4 is an enlarged end elevational view taken substantially on line 4—4 of FIG. 1.

Termination of the fluid pressure application step may be accomplished by operating valve 29 to a blanking position. Following this, the valve 29 may be operated so as to connect the chamber conduit 26 to the vacuum conduit 28, thereby applying suction to the interior of chamber 12. This pulls the tube 16 radially away from the tool 20, freeing the tool, as shown in FIG. 1. Since the inner part of the everting tube 16 has radially the same nominal dimensions as the outer part, it will wrinkle, generally longitudinally (see wrinkles 16a in FIG. 4) and pull tightly against the outer part. This wrinkled, ribbed composite structure is stiff and thus the everting tube 16 stays in place as the tool 20 is pulled back inside it.

The operator may then manually retract the tool 20 a small amount, sufficient to move the tip 23 to a position just behind the annular fold 24, and the valve 29 may then be operated to provide another advancement step, repeating the previously described procedure. These steps may be repeated a sufficient number of times to provide the required distance of movement through the body passage or cavity under study, keeping the tool incremental distance X arbitrarily small, namely such as to provide a satisfactory view of the region just ahead of the everting rim 24 of the device. Thus, in the advancing stroke, the everting tube grips the tool and pulls it along. In the correction stroke, the everting tube grips itself, forms longitudinal ribs, and stays in place clear of the tool as the tool is drawn back.

The device, operated as above described, thus permits continuous examination of the travel path in front of the everting tube. Also, the above-described procedure permits the tool element 20 to be advanced into the body cavity at approximately the same rate as the everting tube.

The above-described device may be employed to introduce a flexible fiber optic bundle and/or tubes and assorted tools into body cavities through openings such as the mouth, nose, anus and urethra. The device keeps the central tool element at or near the folding edge of the everting tube as it progresses into the cavity being examined, and, by means of a fiber optic bundle, which may be employed either solely or combined with an elongated tool, permits continuous visual examination of the path in front of the everting tube.

The configuration of the evertible tube 16 can be such that it grips a substantial surface area of the tool 20, in the manner illustrated in FIG. 2, when fluid pressure is applied to the chamber 12. This gripping action provides reliable concurrent movement of the central tool element 20 and the everting fold 24, and thereby gives efficient control of the insertion of the tool element, as the rectilinear movement of the tool element responsive to the application of fluid pressure is essentially positive and is substantially reproducible as a function of the duration of fluid pressure application during the advancement steps. Combined with this and contributing to the ability to control the tool insertion is the capability of visually examining the region immediately ahead of the everting fold 24 before each advancement step.

While specific embodiments of a method and apparatus for body exploration have been disclosed in the foregoing description, it will be understood that various modifications within the scope of the invention may occur to those skilled in the art. Therefore it is intended that adaptations and modifications should and are intended to be comprehended with the meaning and range of equivalents of the disclosed embodiments. Thus, while the illustrated embodiment can be used as a proctoscope, urethrascope or blood vessel endoscope, depending on its size, it will be understood that the device may be modified or altered to provide many other functions without departing from the invention.

What is claimed is:

1. A method of inserting an elongated tool device having a front end into a body cavity through a body opening comprising
    providing an elongated flexible fluid-impervious tubular element folded inwardly coaxially to form an initial inverted front end portion, the tubular element being connected at one end adjacent a front end of a housing and with a free end of the tubular element being disposed within the housing,
    engaging said tool device substantially axially through the free end of said tubular element and through said flexible tubular element so that the front end of the tool device extends adjacent said initial inverted front end portion,
    subjecting said flexible tubular element externally to positive fluid pressure within said housing to cause the tubular element to collapse about and thereby grip the tool device and to axially advance the tool device while simultaneously everting and advancing axially the front end portion of the tubular element,
    then subjecting said flexible tubular element externally to vacuum so as to release the tool device from said flexible tubular element, retracting the tool device axially rearwardly while maintaining said flexible tubular element in the same axial location, and again subjecting the flexible tubular element to external fluid pressure to repeat the advancement of the tool device.

2. The method of claim 1, and wherein the retraction of the tool device is for a distance approximately equal to one half of its previous increment of advancement.

3. The method of claim 1, and wherein the retraction of the tool device is to a position wherein its front end extends adjacent the inverted front end portion of the flexible tubular element.

4. The method of claim 1, and wherein the starting position of the front end of the tool device is slightly behind the front rim of the initial inverted front end portion of the flexible tubular element.

5. The method of claim 1, and wherein the retraction of the tool device is to a position such that its front end is slightly behind the front rim of the everted portion of the flexible tubular element.

6. An everting tube device comprising an elongated housing including a downstream opening through which to feed a tool device, a flexible evertable tubular member secured to said housing adjacent the downstream opening thereof and folded axially rearwardly through the downstream opening of said housing and extending into said housing, whereby to define a leading fold in said flexible tubular member, an elongated tool device for movement longitudinally through the housing and through the flexible tubular member with its front end adjacent said leading fold of the tubular member, fluid pressure means to pressurize the interior of said housing and vacuum means to draw a vacuum within said housing, means to selectively connect said fluid pressure and vacuum means to the interior of the housing, whereby said tool device and said flexible tubular member are movable longitudinally together when the interior of said housing is pressurized, and said tool device is retractable while said flexible tubular member is stationary when the interior of said housing is under vacuum.

7. The everting tube device of claim 6, and wherein said tool device includes fiber optic means to view the interior of a body cavity extending out of the end of the housing opposite the downstream opening of said housing.

8. The everting tube device of claim 6, and means, located on the portion of the flexible tubular member inside said housing, to surround and slidably and sealingly engage said tool device.

9. The everting tube device of claim 6, and wherein said tool element includes a fiber optic bundle extending out of the end of the housing opposite the downstream opening and being provided with viewing means to look into and through said fiber optic bundle.

10. The everting tube device of claim 9, and wherein the rear portion of the flexible tubular member inside the housing is provided with a bushing surrounding and slidably and sealingly engaging said tool element.

11. A device for feeding an elongated tool into an elongated cavity, comprising:
    an elongated housing having an upstream opening and a downstream opening through which to feed the elongated tool,
    a flexible evertible elongated tube secured to said housing adjacent the downstream opening thereof and inverted axially rearwardly inside itself and through the downstream opening of said housing and extending into said housing, thereby defining a leading fold in said flexible tubular member extending beyond the downstream opening of said housing, and said flexible tubular member defining a free end with said housing,
    a sealing member disposed at the free end of said flexible tubular member lying within said housing, said sealing member being adapted to sealingly and slidably engage the elongated tool,
    means to collapse said flexible tubular member about and thereby grip the elongated tool and to simultaneously axially advance the tool while axially everting the flexible tubular member and advancing the leading fold thereof, said means including means to pressurize the interior of said housing, and
    means to retract the tool while leaving said flexible tubular element in its advanced axial position, said means including means to draw a vacuum within said housing to cause said flexible tubular member to release its grip on the elongated tool to permit the tool to be retracted rearwardly relative to said sealing means at the free end of said tube, while said tube remains in its axial position.

* * * * *